United States Patent
Mccormick et al.

(10) Patent No.: US 10,973,597 B2
(45) Date of Patent: Apr. 13, 2021

(54) MULTI-INPUT ROBOT SURGICAL SYSTEM CONTROL SCHEME

(71) Applicant: Covidien LP, Mansfield, MA (US)

(72) Inventors: James Mccormick, Barrington, RI (US); Gabriel McHugh, Braintree, MA (US); William Peine, Ashland, MA (US); Renen Bassik, Lexington, MA (US)

(73) Assignee: COVIDIEN LP, Mansfield, MA (US)

( * ) Notice: Subject to any disclaimer, the term of this patent is extended or adjusted under 35 U.S.C. 154(b) by 339 days.

(21) Appl. No.: 15/770,038

(22) PCT Filed: Oct. 20, 2016

(86) PCT No.: PCT/US2016/057788
§ 371 (c)(1),
(2) Date: Apr. 20, 2018

(87) PCT Pub. No.: WO2017/070269
PCT Pub. Date: Apr. 27, 2017

(65) Prior Publication Data
US 2018/0311005 A1    Nov. 1, 2018

Related U.S. Application Data

(60) Provisional application No. 62/244,845, filed on Oct. 22, 2015.

(51) Int. Cl.
*A61B 17/28* (2006.01)
*A61B 34/37* (2016.01)
(Continued)

(52) U.S. Cl.
CPC .............. *A61B 34/37* (2016.02); *A61B 17/28* (2013.01); *A61B 17/32* (2013.01); *A61B 34/25* (2016.02);
(Continued)

(58) Field of Classification Search
CPC ...... H04L 67/12; G06N 20/00; G05B 13/028; B25J 19/02; B25J 9/1679; B25J 11/008;
(Continued)

(56) References Cited

U.S. PATENT DOCUMENTS 6,402,737 B1    6/2002  Tajima et al.
6,459,926 B1 *  10/2002 Nowlin .................. A61B 34/70
                                                    600/102

(Continued)

FOREIGN PATENT DOCUMENTS

CN    1591287 A     3/2005
WO    2006052375 A2  5/2006

OTHER PUBLICATIONS

Ma et al., Design and optimization of manipulator for laparoscopic minimally invasive surgical robotic system, 2012, IEEE, p. 598-603 (Year: 2012).*

(Continued)

*Primary Examiner* — McDieunel Marc (57) ABSTRACT

For controlling a robotic surgical system including arms, consoles, and a controller in communication with the arms and consoles, systems and methods are provided that include receiving a request for selection of a first arm for assignment to a first console, and in response to the request, determining whether the first arm is already assigned, assigning the first arm to the first console, if a determination is made that the first arm is not already assigned, determining whether the first arm is to be deselected from a previous assignment, if a determination is made that the first arm is already assigned, generating an error message, if a determination is made that the first arm is not to be deselected, and deselecting the first arm from the previous assignment and assigning the first arm to the first console, if a determination is made that the first arm is to be deselected.

19 Claims, 8 Drawing Sheets

(51) Int. Cl.
*A61B 34/00* (2016.01)
*A61B 17/32* (2006.01)
*B25J 11/00* (2006.01)
*B25J 13/06* (2006.01)

(52) U.S. Cl.
CPC ............. *B25J 11/008* (2013.01); *B25J 13/06* (2013.01); *A61B 2017/2808* (2013.01); *A61B 2560/0475* (2013.01); *A61B 2560/0487* (2013.01)

(58) Field of Classification Search
CPC ... B25J 9/1689; B25J 9/00; B25J 13/06; B25J 5/00; B25J 9/1697; B25J 3/04; B25J 19/023; B25J 13/025; B25J 9/1692; B25J 11/0005; B25J 15/0253; B25J 19/022; B25J 21/00; B25J 3/00; B25J 5/007; B25J 9/0003; B25J 9/1602; B25J 9/1615; B25J 9/162; B25J 9/163; H04W 4/38; H04W 84/20; B60P 3/007; B60W 10/04; G05D 1/0011; G06T 7/0004; G06T 2207/10016; G06T 2207/10068; G06T 2207/10072; G06T 2207/20092; G06T 7/20; A61B 34/30; A61B 5/11; A61B 34/37; A61B 34/25; A61B 90/361; A61B 5/0024; A61B 34/35; A61B 17/32; A61B 1/00006; A61B 2017/00199; A61B 2017/320071; A61B 2018/00642; A61B 2018/00916; A61B 2018/00922; A61B 2560/0487; A61B 34/10; A61B 34/70; A61B 34/76; A61B 5/00; A61B 90/37; A61B 2090/064; A61B 34/77; A61B 2034/305; A61B 34/71; A61B 2017/00477; A61B 2018/00982; A61B 34/74; A61B 17/00234; A61B 1/00193; A63B 2220/803; A63B 2220/806; A63B 2034/301; A63B 2090/371; A63B 2090/506; A63B 34/72; A63B 90/36; A63B 2017/2943; A63B 17/29; A63B 2017/00017; G09B 19/24; G09B 23/28; G09B 2017/00207; G09B 2017/00725; G09B 2017/00911; G09B 2034/102; G09B 2034/2059; G09B 2090/066; G09B 2090/363; G09B 2090/374; G09B 34/20; G09B 34/75; G09B 90/06; G09B 90/20; G09B 90/25; G09B 90/39; E04H 15/28
See application file for complete search history.

(56) References Cited

U.S. PATENT DOCUMENTS

| | | | |
|---|---|---|---|
| 6,728,599 B2* | 4/2004 | Wang | A61B 34/70 128/897 |
| 6,837,883 B2 | 1/2005 | Moll et al. | |
| 6,933,695 B2 | 8/2005 | Blumenkranz | |
| 7,155,316 B2* | 12/2006 | Sutherland | A61B 90/25 700/248 |
| 7,979,157 B2* | 7/2011 | Anvari | A61G 13/10 700/245 |
| 7,983,793 B2 | 7/2011 | Toth et al. | |
| 8,418,073 B2* | 4/2013 | Mohr | A61B 1/00009 715/764 |
| 2002/0082612 A1* | 6/2002 | Moll | G09B 23/285 606/130 |
| 2002/0128552 A1* | 9/2002 | Nowlin | A61B 34/37 600/427 |
| 2006/0047365 A1 | 3/2006 | Ghodoussi et al. | |
| 2006/0149418 A1* | 7/2006 | Anvari | A61G 13/10 700/245 |
| 2006/0178559 A1 | 8/2006 | Kumar et al. | |
| 2007/0147707 A1* | 6/2007 | Coste-Maniere | A61B 5/055 382/298 |
| 2009/0234371 A1 | 9/2009 | Tierney et al. | |
| 2010/0217991 A1 | 8/2010 | Choi | |
| 2010/0228249 A1* | 9/2010 | Mohr | A61B 18/1206 606/41 |
| 2010/0234857 A1* | 9/2010 | Itkowitz | A61B 34/77 606/130 |
| 2018/0185110 A1* | 7/2018 | Kumar | A61B 34/30 |
| 2019/0038335 A1* | 2/2019 | Mohr | A61B 18/12 |

OTHER PUBLICATIONS

Du et al., Design Optimization of a Minimally Invasive Surgical Robot, 2007, IEEE, p. 179-184 (Year: 2007).*
SuKhoon et al., Design of Master Console Robot for Natural Orifice Transluminal Endoscopic Surgery, 2009, IEEE, 1152-1157 (Year: 2009).*
Lago et al., From Laparoscopic Surgery to 3-D Double Console Robot-Assisted Surgery, 2010, IEEE, p. 1-4 (Year: 2010).*
Konietschke et al., A multimodal training platform for minimally invasive robotic surgery, 2010, IEEE, p. 422-427 (Year: 2010).*
Low et al., A review of master-slave robotic systems for surger, 2005, IEEE, p. 37-42 (Year: 2005).*
Extended European Search Report dated Jun. 12, 2019 corresponding to counterpart Patent Application EP 16858172.6.
Int'l Search Report and Written Opinion of counterpart Int'l Appln PCT/US2016/057788 dated Feb. 3, 2017.
Chinese First Office Action dated Apr. 1, 2020 corresponding to counterpart Patent Application CN 201680059839.
Chinese Office Action for application No. 201680059839X dated Oct. 23, 2020 with English translation.

* cited by examiner

MULTI-INPUT ROBOT SURGICAL SYSTEM CONTROL SCHEME

CROSS-REFERENCE TO RELATED APPLICATIONS

This application is a U.S. National Stage Application filed under 35 U.S.C. § 371(a) of International Patent Application Serial No. PCT/US2016/057788, filed Oct. 20, 2016, which claims the benefit of and priority to U.S. Provisional Patent Application Ser. No. 62/244,845, filed Oct. 22, 2015, the entire disclosure of which is incorporated by reference herein.

BACKGROUND

Robotic surgical systems are increasingly being used to perform minimally invasive medical procedures. Typically during such medical procedures, a clinician is positioned at a console remote from the robotic surgical system. The clinician provides input to a user interface at the console to thereby control the robotic surgical system. For example, the clinician moves an input controller or handle to manipulate an end effector that acts on a patient.

In some configurations of the robotic surgical system, multiple consoles are included to allow multiple clinicians to manipulate the system. In this regard, each of the consoles includes a user interface, which can be used to control the same end effectors. However, allowing multiple users to control the same end effector increases the need for coordinated cooperation between the clinicians and may reduce efficiency. Thus, there is a need for a robotic surgical system configured to be used with multiple consoles to allow each user to provide an input without interfering with another. Additionally, there is a need for the robotic surgical system to be operable by multiple clinicians while improving efficiencies during robotic surgical procedures.

SUMMARY

In an aspect of the present disclosure, a method of controlling a robotic surgical system is provided, the robotic surgical system including a plurality of arms, a plurality of consoles, and a controller in communication with the plurality of arms and the plurality of consoles. The method includes receiving a request for selection of a first arm from the plurality of arms for assignment to a first console of the plurality of consoles, in response to the request, determining whether the first arm is already assigned, assigning the first arm to the first console, if a determination is made that the first arm is not already assigned, and determining whether the first arm is to be deselected from a previous assignment, if a determination is made that the first arm is already assigned. The method also includes generating an error message, if a determination is made that the first arm is not to be deselected, and deselecting the first arm from the previous assignment and assigning the first arm to the first console, if a determination is made that the first arm is to be deselected.

In another aspect of the present disclosure, the method further includes placing the plurality of consoles in a hold mode, prior to receiving the request for selection.

In still another aspect of the present disclosure, in the method, the placing the plurality of consoles in the hold mode includes determining whether any arm of the plurality of arms is assigned to any of the consoles of the plurality of consoles and deselecting the assigned arms from the consoles.

In another aspect of the present disclosure, the method further includes receiving a request for selection of a second arm from the plurality of arms for assignment to a second console of the plurality of consoles, in response to the request, determining whether the second arm is already assigned, determining whether the second arm is to be deselected, if a determination is made that the second arm is already assigned, assigning the second arm to the second console, if a determination is made that the second arm is not already assigned, generating an error message, if a determination is made that the second arm is not to be deselected, and deselecting the second arm and assigning the second arm to the second console, if a determination is made that the second arm is to be deselected.

In another aspect of the present disclosure, in the method, the receiving the request for selection includes receiving the request for selection from the first console.

In another aspect of the present disclosure, in the method, the receiving the request for selection includes receiving the request for selection from a remote computer.

According to another aspect of the present disclosure, a robotic surgical system is provided and includes a plurality of linkages moveably coupled to a base, a plurality of consoles each including an input device, a processing unit in communication with the plurality of consoles and operatively associated with the plurality of linkages, and a memory coupled to the processing unit. The memory includes instructions that, when executed by the processing unit, causes the processing unit to receive a request for selection of a first linkage from the plurality of linkages for assignment to a first console of the plurality of console, in response to the request, determine whether the first linkage is already assigned, assign the first arm to the first console, if a determination is made that the first linkage is not already assigned, determine whether the first linkage is to be deselected from a previous assignment, if a determination is made that the first linkage is already assigned, generate an error message, if a determination is made that the first linkage is not to be deselected, and deselect the first linkage from the previous assignment and assigning the first linkage to the first console, if a determination is made that the first linkage is to be deselected.

In an aspect of the present disclosure, the memory further includes instructions that, when executed by the processing unit, causes the processing unit to place the plurality of consoles in a hold mode, prior to the receiving the request for selection.

In an aspect of the present disclosure, the memory further includes instructions that, when executed by the processing unit, causes the processing unit to place the plurality of consoles in the hold mode including determining whether any arm of the plurality of arms is assigned to any of the consoles of the plurality of consoles and deselecting the assigned arms from the consoles.

In an aspect of the present disclosure, the memory further includes instructions that, when executed by the processing unit, causes the processing unit to receive a request for selection of a second arm from the plurality of arms for assignment to a second console of the plurality of consoles, in response to the request, determine whether the second arm is already assigned, determine whether the second arm is to be deselected, if a determination is made that the second arm is already assigned, assign the second arm to the second console, if a determination is made that the second arm is not already assigned, generate an error message, if a determination is made that the second arm is not to be deselected, and deselect the second arm and assigning the second arm to the second console, if a determination is made that the second arm is to be deselected.

In an aspect of the present disclosure, the receiving the request for selection includes receiving the request for selection from the first console.

In an aspect of the present disclosure, the receiving the request for selection includes receiving the request for selection from a remote computer.

In accordance with another aspect of the present disclosure, a non-transitory computer-readable medium is provided including instructions that, when executed by a processor, causes the processor to receive a request for selection of a first linkage from the plurality of linkages for assignment to a first console of the plurality of consoles, in response to the request, determine whether the first linkage is already assigned, assign the first arm to the first console, if a determination is made that the first linkage is not already assigned, determine whether the first linkage is to be deselected from a previous assignment, if a determination is made that the first linkage is already assigned, generate an error message, if a determination is made that the first linkage is not to be deselected, and deselect the first linkage from the previous assignment and assigning the first linkage to the first console, if a determination is made that the first linkage is to be deselected.

In an aspect of the present disclosure, the non-transitory computer-readable medium further includes instructions that, when executed by the processing unit, causes the processing unit to place the plurality of consoles in a hold mode, prior to the receiving the request for selection.

In an aspect of the present disclosure, the non-transitory computer-readable medium further includes instructions that, when executed by the processing unit, causes the processing unit to place the plurality of consoles in the hold mode including determining whether any arm of the plurality of arms is assigned to any of the consoles of the plurality of consoles and deselecting the assigned arms from the consoles.

In an aspect of the present disclosure, the non-transitory computer-readable medium further includes instructions that, when executed by the processing unit, causes the processing unit to receive a request for selection of a second arm from the plurality of arms for assignment to a second console of the plurality of consoles, in response to the request, determine whether the second arm is already assigned, determine whether the second arm is to be deselected, if a determination is made that the second arm is already assigned, assign the second arm to the second console, if a determination is made that the second arm is not already assigned, generate an error message, if a determination is made that the second arm is not to be deselected, and deselect the second arm and assigning the second arm to the second console, if a determination is made that the second arm is to be deselected.

In an aspect of the present disclosure, the receiving the request for selection includes receiving the request for selection from the first console.

In an aspect of the present disclosure, the receiving the request for selection includes receiving the request for selection from a remote computer.

Robotic arms of robotic surgical systems may be selectively controlled by users operating one or more user inputs at one or more consoles. An assignment of which robotic arms are controlled by which consoles may be identified.

Control of a first of the robotic arms may be assigned to a first console in response to receiving a request to do so when the first robotic arm is not identified as assigned to at least one of the consoles. Control of the first robotic arm may be deassigned from any assigned consoles after a respective assigned console is in a hold mode responsive to receiving the request when the first robotic arm is identified as currently assigned to at least one of the consoles other than the first console. The system may wait until control of the first robotic arm has been deassigned from each of the currently assigned consoles before the system assigns control of the first robotic arm to the first console as specified in the request to do so.

Further details and aspects of exemplary embodiments of the present disclosure are described in more detail below with reference to the appended figures.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Figure 1:
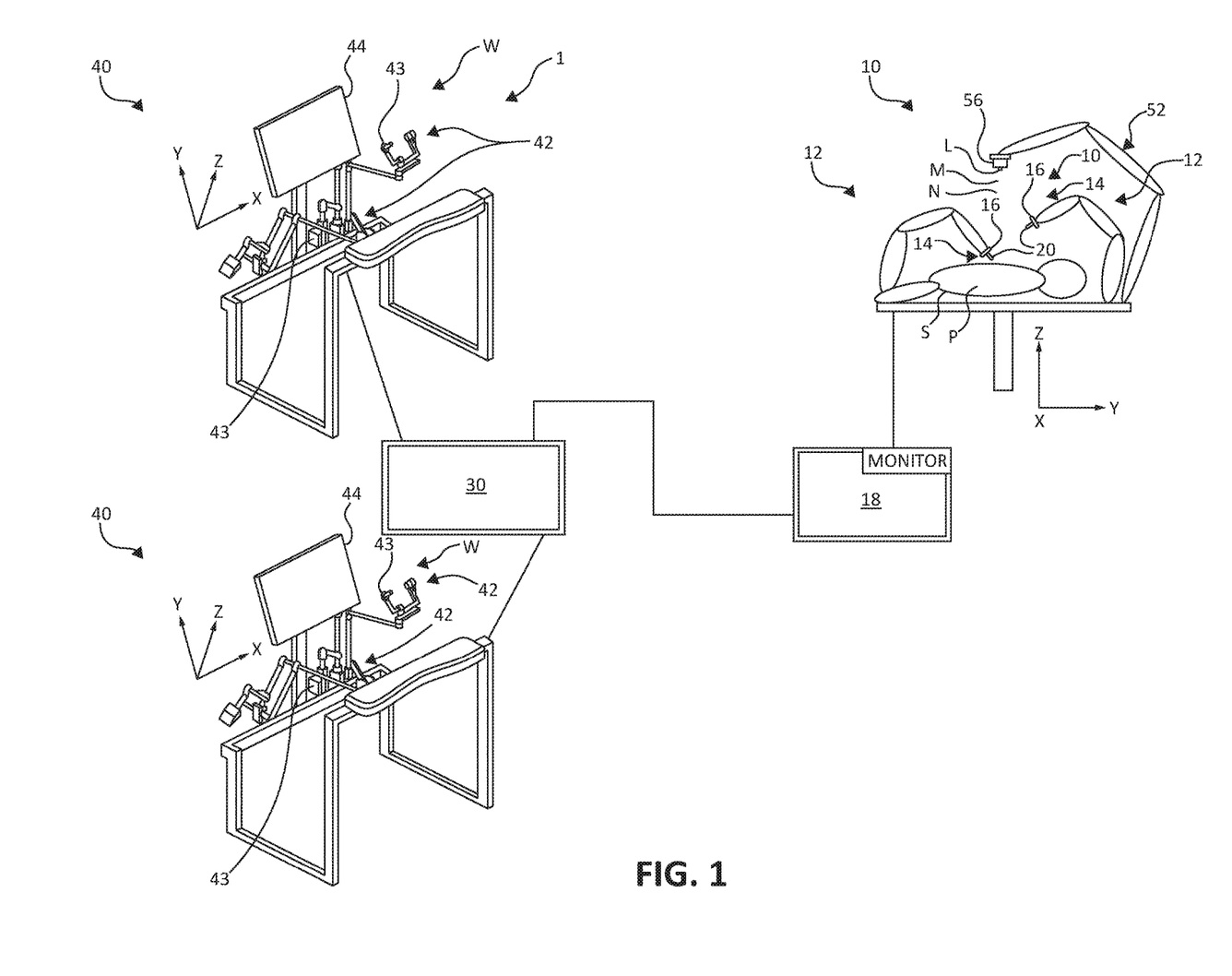
FIG. 1 is a schematic illustration of a multi-input robotic surgical system in accordance with an embodiment.

Referring to FIG. 1, a multi-input robotic surgical system 1 in accordance with the present disclosure is shown generally and includes a robotic system 10, a processing unit 30, and user interfaces 40. The robotic system 10 generally includes linkages 12 and a robot base 18. Each of the linkages 12, which may be in the form of arms, has an end 14 that moveably supports an end effector or tool 20 configured to act on tissue. The ends 14 of the arms 12 may include an imaging device 16 for imaging a surgical site "S".

Each user interface 40 communicates with the robot base 18 through the processing unit 30 and includes a display device 44 which is configured to display images. In accordance with an embodiment, the display device 44 displays three-dimensional images of the surgical site "S" which may include data captured by imaging devices 16 and/or include data captured by imaging devices (not shown) that are positioned about the surgical theater (e.g., an imaging device positioned within the surgical site "S"), an imaging device positioned adjacent the patient "P", or an imaging device 56 positioned at a distal end of an imaging arm 52). The imaging devices (e.g., imaging devices 16, 56) may capture visual images, infra-red images, ultrasound images, X-ray images, thermal images, and/or any other known real-time images of the surgical site "S". The imaging devices transmit captured imaging data to the processing unit 30 which creates three-dimensional images of the surgical site "S" in real-time from the imaging data and transmits the three-dimensional images to the display device 44 for display. In another embodiment, the displayed images are two-dimensional renderings of the data captured by the imaging devices.

The user interface 40 includes input devices 42 to allow a clinician to manipulate the robotic system 10 (e.g., move the arms 12, the ends 14 of the arms 12, and/or the tools 20). Each of the input devices 42 communicates with the processing unit 30 to transmit control signals thereto and to receive feedback signals therefrom. Additionally or alternatively, each of the input handles 42 may include control interfaces (not shown) which allow the surgeon to manipulate (e.g., clamp, grasp, fire, open, close, rotate, thrust, slice, etc.) the tools 20 supported at the ends 14 of the arms 12.

In an embodiment, the input devices 42 are handles that are each moveable through a predefined workspace "W" to move the ends 14 of the arms 12 within a surgical site "S". It will be appreciated that while the workspace "W" is shown in two-dimensions in FIG. 2, the workspace "W" is a three-dimensional workspace. The three-dimensional images on the display device 44 are oriented such that the movement of the input device 42 moves the ends 14 of the arms 12 as viewed on the display device 44. It will be appreciated that the orientation of the three-dimensional images on the display device may be mirrored or rotated relative to view from above the patient "P". In addition, it will be appreciated that the size of the three-dimensional images on the display device 44 may be scaled to be larger or smaller than the actual structures of the surgical site permitting the surgeon to have a better view of structures within the surgical site "S". As the input devices 42 are moved, the tools 20 are moved within the surgical site "S" as detailed below. Movement of the tools 20 may also include movement of the ends 14 of the arms 12 which support the tools 20. Although illustrated as a handle, a handle including a clutch switch, one or more of the input devices 42 may be a touchpad, joystick, keyboard, mouse, or other computer accessory, and/or a foot switch, pedal, trackball, or other actuatable device configured to translate physical movement from the clinician to signals sent to the processing unit 30.

The movement of the tools 20 is scaled relative to the movement of the input handles 42. When the input handles 42 are moved within a predefined workspace "W", the input handles 42 send control signals to the processing unit 30. The processing unit 30 analyzes the control signals to move the tools 20 in response to the control signals. The processing unit 30 transmits scaled control signals to the robot base 18 to move the tools 20 in response the movement of the input handles 42.

Figure 2:
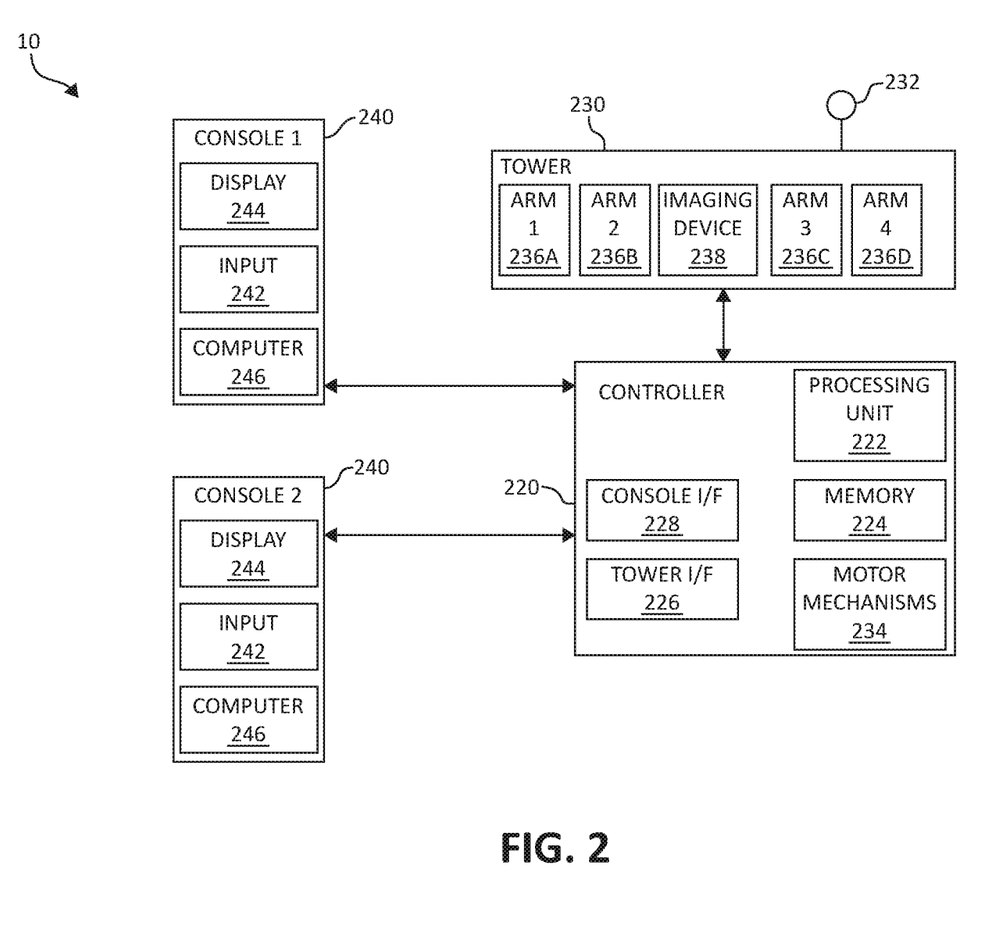
FIG. 2 is a functional block diagram of the system architecture for controlling the multi-input robotic surgical system of FIG. 1.

FIG. 2 is simplified block diagram of the robotic surgical system 10 of FIG. 1. The robotic surgical system 10 includes a controller 220, a tower 230, and consoles 240. The controller 220 is configured to communicate with the tower 230 to thereby provide instructions for operation, in response to input received from one of the consoles 240.

The controller 230 generally includes a processing unit 222, a memory 224, a tower interface 226, and a consoles interface 228. The processing unit 222, in particular by means of a computer program stored in the memory 224, functions in such a way to cause components of the tower 230 to execute a desired movement according to a movement defined by input devices 242 of the consoles 240. In this regard, the processing unit 222 includes any suitable logic control circuit adapted to perform calculations and/or operate according to a set of instructions. The processing unit 222 may include one or more processing devices, such as a microprocessor-type of processing device or other physical device capable of executing instructions stored in the memory 224 and/or processing data. The memory 224 may include transitory type memory (e.g., RAM) and/or non-transitory type memory (e.g., flash media, disk media, etc.). The tower interface 226 and consoles interface 228 communicate with the tower 230 and consoles 240, respectively, either wirelessly (e.g., Wi-Fi, Bluetooth, LTE, etc.) and/or via wired configurations. Although depicted as separate modules, the interfaces 232, 234 are a single component in other embodiments.

The tower 230 includes a communications interface 232 configured to receive communications and/or data from the tower interface 226 for manipulating motor mechanisms 234 to thereby move arms 236a-d. In accordance with an embodiment, the motor mechanisms 234 are configured to, in response to instructions from the processing unit 222, receive an application of current for mechanical manipulation of cables (not shown) which are attached to the arms 236a-d to cause a desired movement of a selected one of the arms 236a-d and/or an instrument coupled to an arm 236a-d. The tower 230 also includes an imaging device 238, which captures real-time images and transmits data representing the images to the controller 230 via the communications interface 232.

To manipulate the devices of the tower 230, each console 240 has an input device 242, a display 244, and a computer 246. The input device 242 is coupled to the computer 246 and is used by the clinician to provide an input. In this regard, the input device 242 may be a handle or pedal, or a computer accessory, such as a keyboard, joystick, mouse, button, touch screen, switch, trackball or other component. The display 244 displays images or other data received from the controller 220 to thereby communicate the data to the clinician. The computer 246 includes a processing unit and memory, which includes data, instructions and/or information related to the various components, algorithms, and/or operations of the tower 230 and can operate using any suitable electronic service, database, platform, cloud, or the like.

Figure 3:
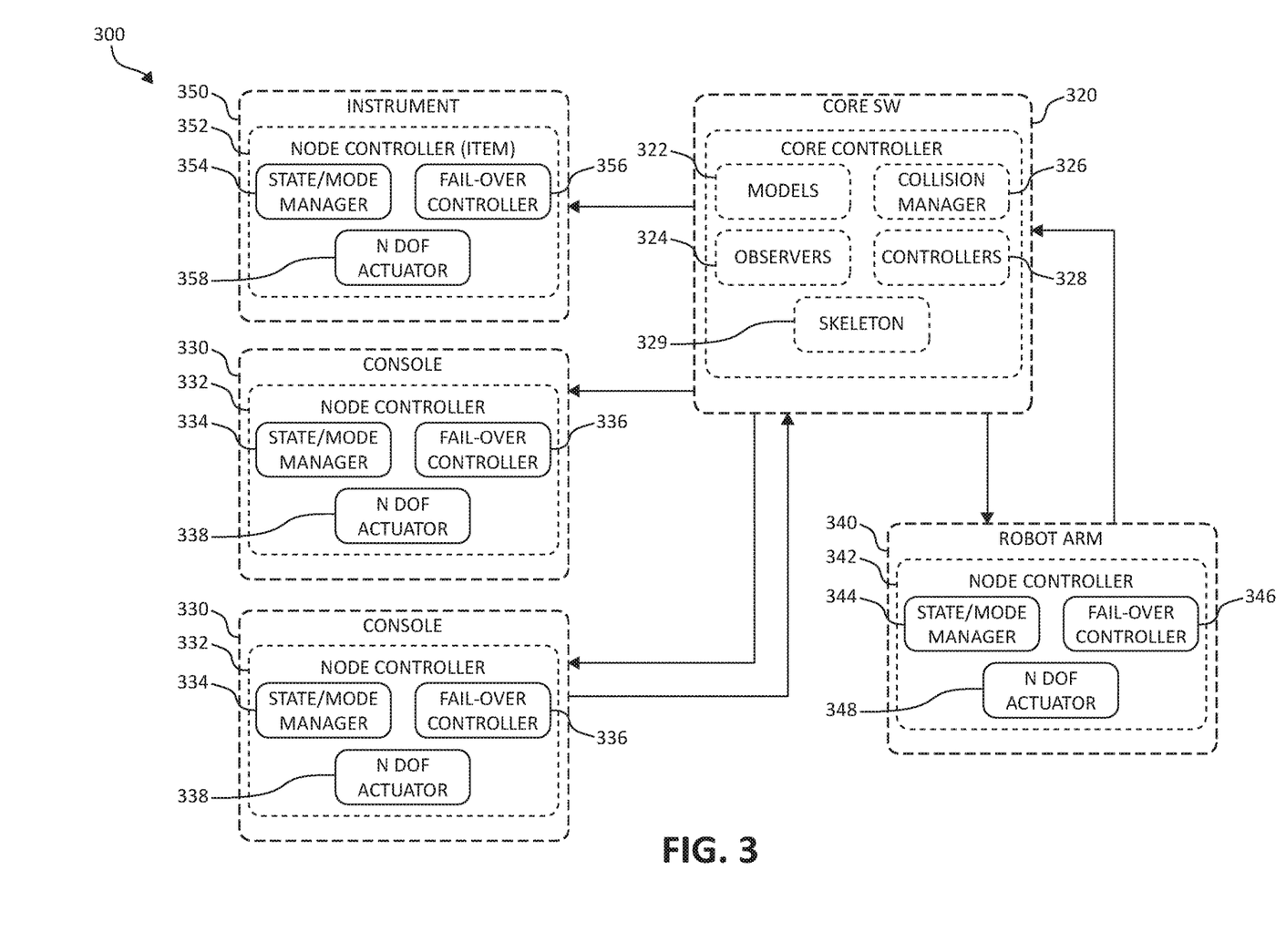
FIG. 3 is a block diagram of the control components for controlling the multi-input robotic surgical system of FIG. 1.

FIG. 3 is a simplified functional block diagram of a system architecture 300 of the robotic surgical system 10 included in FIG. 2. The system architecture 300 includes a core module 320, console modules 330, a robot arm module 340, and an instrument module 350. The core module 320 serves as a central controller for the robotic surgical system 10 and coordinates operations of all of the other modules 330, 340, 350. For example, the core module 320 maps control devices to the arms 14, determines a current status of the system 10, performs all kinematics and frame transformations, and relays resulting movement commands. In this regard, the core module 320 receives and analyzes data from each of the other modules 330, 340, 350 in order to provide instructions or commands to the other modules 330, 340, 350 for execution within the robotic surgical system 10. Although depicted as separate modules, two or more of the modules 320, 330, 340, and 350 are combined as a single component in other embodiments.

The core module 320 includes models 322, observers 324, a collision manager 326, controllers 328, and a skeleton 329. The models 322 include units that provide abstracted representations (base classes) for controlled components, such as the motors 18 and/or the arms 12. The observers 324 create state estimates based on input and output signals received from the other modules 330, 340, 350. The collision manager 326 prevents collisions between components that have been registered within the system 10. The skeleton 329 tracks the system 10 from a kinematic and dynamics point of view. For example, the kinematics item may be implemented either as forward or inverse kinematics, in an embodiment. The dynamics item may be implemented as algorithms used to model dynamics of the system's components.

Each console module 330 communicates with surgeon control devices at corresponding consoles 240 and relays inputs received from the console 240 to the core module 320. In accordance with an embodiment, the console module 330 communicates button status and control device positions to the core module 320 and includes a node controller 332 that includes a state/mode manager 334, a fail-over controller 336, and a N degree of freedom ("DOF") actuator 338.

The robot arm module 340 coordinates operation of a robot arm subsystem, an arm cart subsystem, a set up arm, and an instrument subsystem in order to control movement of a corresponding arm 12. It will be appreciated that the robot arm module 340 corresponds to and controls a single arm. As such, although a single robot arm module 340 is shown, additional modules 340 are included for each of the arms 236a-d, in an embodiment. Each robot arm module 340 includes a node controller 342, a state/mode manager 344, a fail-over controller 346, and a N degree-of-freedom ("DOF") actuator 348.

The instrument module 350 controls movement of a tool 20 (shown in FIG. 2) attached to the arm 12 (also shown in FIG. 2). The instrument module 350 is configured to correspond to and control a single tool. Thus, in configurations in which multiple tools are included, additional instrument modules 350 are likewise included. In an embodiment, the instrument module 350 obtains and communicates data related to the position of tool 20 on the arm 12. Each instrument module 350 has a node controller 352, a state/ mode manager 354, a fail-over controller 356, and a N degree-of-freedom ("DOF") actuator 358.

Figure 4:
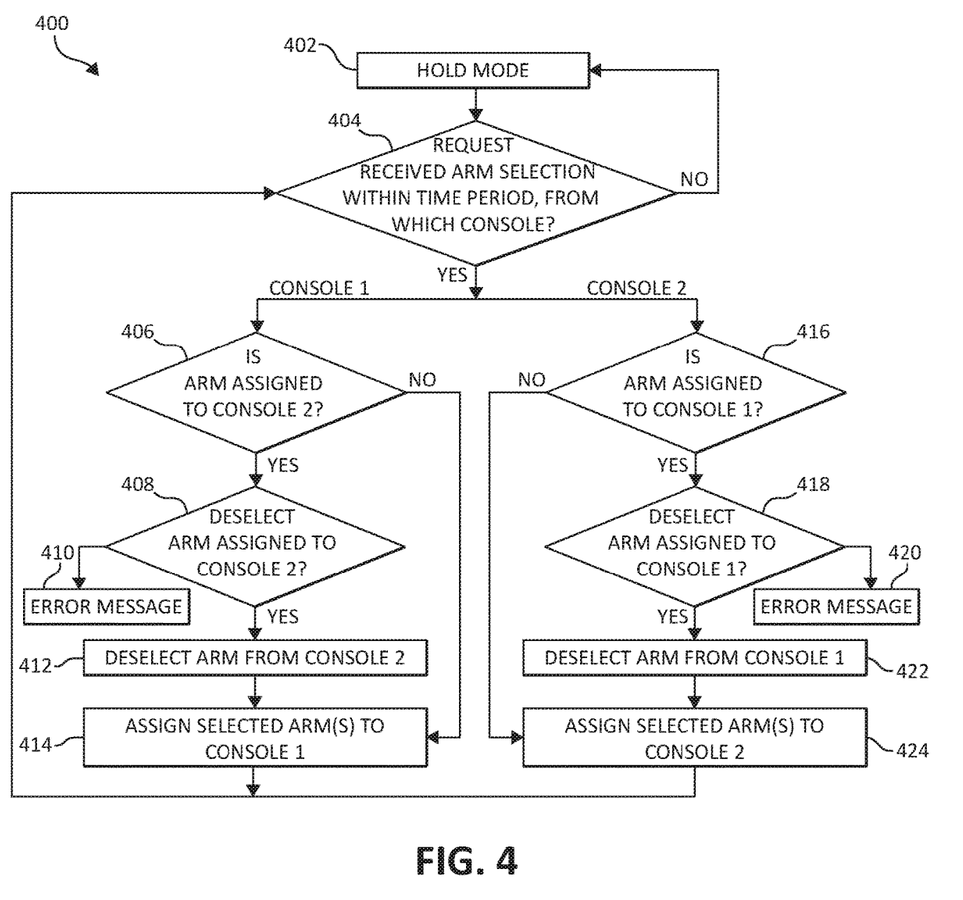
FIG. 4 is a flow diagram of a process for controlling the multi-input robotic surgical system of FIG. 1.

As noted briefly above, the consoles are configured to be operated concurrently to allow more than one clinician to provide input to the robot system 10 and to manipulate the arms 236a-d. For example, a clinician at one console 240 may provide input to one input 242, while another clinician may be situated at another console 240 to provide input to another input 242. FIG. 4 is a flow diagram of a control process 400 for operating a multi-input surgical system, in accordance with an embodiment. The control process 400 prevents the multiple clinicians from attempting to control the same arm, for example, arm 236a-d of the tower 230.

At initiation of the control process 400, each console 240 is placed in a hold mode, at step 402. In an embodiment, the hold mode is a default mode after a power up, a reset, a reboot of the system, or after another initiating operation of the system. During the hold mode, the arms 236a-d are unassigned to any console 240. According to an embodiment, in an event that any of the arms 236a-d are already assigned to a console, the arms 236-d are deselected and unassigned.

Next, a request is received from a console indicating that the clinician at the console has made an arm selection at step 404. For example, the clinician at one of the consoles may use the input 242 to make the arm selection via a keyboard, mouse, joystick or other input 242, such as by typing a selection or selecting an icon or other representation from a drop down menu illustrating arms 236a-d which may be selected. In another example, the consoles 1 and 2 may not be occupied by a user during the time of arm selection, and hence, the signal to assign the one or more arms 236a-d to console 1 occurs remotely from another computer. In any event, if no signal has been received or the signal has been received but the clinician has not made a selection within a predetermined time period, the consoles 1, 2 remain in the hold mode at step 402. As part of the request, a determination is made as to whether the arm selection request originates from console 1 or console 2.

If the received input indicates that one or more of the arms 236a-d has been selected for assignment to console 1 and the predetermined time period has not elapsed, a determination is then made as to whether the selected arms to be assigned to console 1 are already assigned to console 2 at step 406. If not, the selected arms are assigned to console 1 at step 414. If so, a determination is made as to whether to deselect the arm assigned to console 2 at step 408. Deselection may occur automatically, for example, as a result of a prioritization of clinician privileges or console usage privileges. Alternatively, deselection occurs by a manual override in which a clinician having administrator privileges deselects the arms. If the already-assigned arm(s) are not to be deselected, an error message is communicated at 410. The error message may be communicated to the clinician attempting to select the already-assigned arm and/or to the clinician at the console to which the arm has already been assigned. A flashing message on one or both of the displays 244, an audible tone, a vibration, or other signal is used to alert the clinician(s) that the arms are unavailable for assignment.

If the arm(s) are to be deselected, the arm is deselected at step 412 and is then assigned to console 1 at step 414. In an embodiment, once assigned, the arm can only be operated by the clinician at console 1, and the clinician at console 2 is unable to control the arm unless it becomes deselected. In another embodiment, override protocols are included such that, if initiated, the clinician at console 2 can overtake control of the arm, even if the arm has not been deselected.

Returning to step 404, if a signal is received indicating that an input has been received that an arm selection has been made at console 2, a determination is then made as to whether the selected arm is already assigned to console 1 at step 416. If not, the selected arms are assigned to console 1 at step 424. If so, a determination is made as to whether to deselect the already-assigned arm from console 1 at step 418. As noted above, the determination to deselect the arm is an automatic response due to priority of the clinician privilege or console usage privilege, or a manual input received from the clinician. If the arm is not to be deselected, an error message is communicated at 420. An error message, such as a flashing message on the displays of one or both of the consoles 1 or 2, an audible tone, a vibration, or another alert signal, is communicated to the clinician. If the arm is to be deselected, the arm is deselected at step 422 and is then assigned to console 2 at step 424. In an embodiment, once assigned, the arm can only be operated by the clinician at console 2, and the clinician at console 1 is unable to control the arm unless it becomes deselected. In another embodiment, override protocols are included such that, if initiated, the clinician at console 1 overtakes control of the arm, even if it has not been deselected.

After step 414 or 424, the method 400 iterates at step 404. It will be appreciated that as part of the assignment of the arms, the displays and input signals, such as foot switch signals or clutch signals, also operate normally for each clinician of the assigned arms. Control of the imaging device 238 associated with an arm is also assigned with the assigned arm. For example, assignment of the imaging device 238 occurs in a similar manner as the assignment of the arms. In an embodiment in which the arm assignments are divided between both console 1 and console 2, if the imaging device 238 has not already been assigned to one of the consoles, a clinician at one of the consoles 1, 2 can select the imaging device 238 for assignment to his or her console 1, 2.

Figure 5:
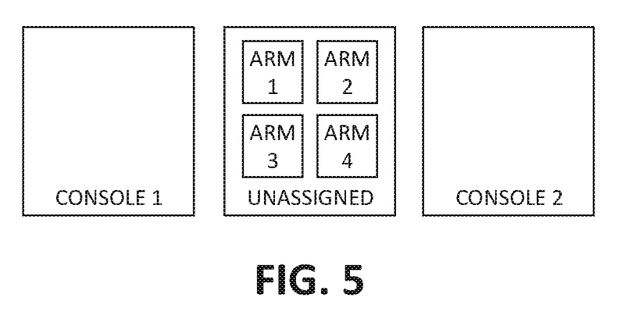
FIGS. 5 through 10 are simplified block diagrams illustrating selection and deselection of arms by each console according to the process illustrated in FIG. 4 in accordance with an embodiment.
Figure 6:
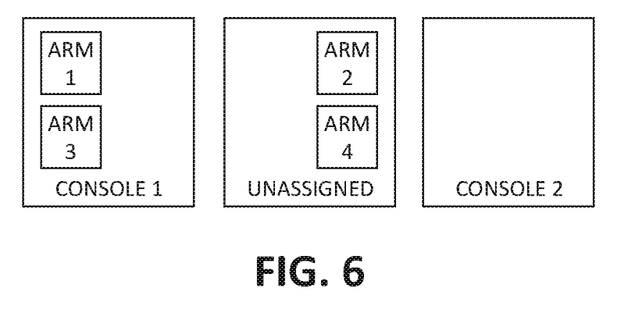

Turning now to FIGS. 5-10, simplified block diagrams illustrating the process of assigning the arms to the consoles are provided. FIG. 5 is a representation of the system 10 in a hold mode. As noted above, none of arms 1-4 are assigned to a console during the hold mode. In an embodiment, arms 1 and 3 are selected to be assigned to console 1. Hence, a determination is made as to whether arms 1 and 3 have already been assigned to console 2. If arms 1 and 3 have not been assigned, they are assigned to console 1, as shown in FIG. 6. As arms 2 and 4 were not selected to be assigned to console 1, arms 2 and 4 remain unassigned while console 2 has no arms assigned.

Figure 7:
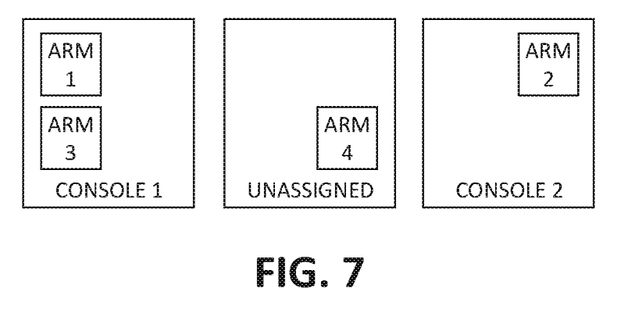

In an embodiment, arm 2 is selected to be assigned to console 2. After a determination is made that arm 2 is not assigned to console 1 (as shown in FIG. 6), system 10 assigns arm 2 to console 2 as illustrated in FIG. 7. Arm 4 remains unassigned.

Figure 8:
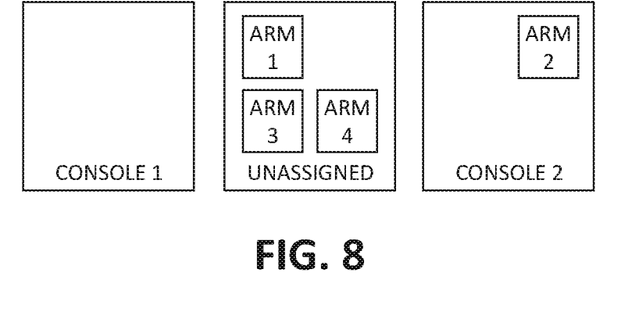
Figure 9:
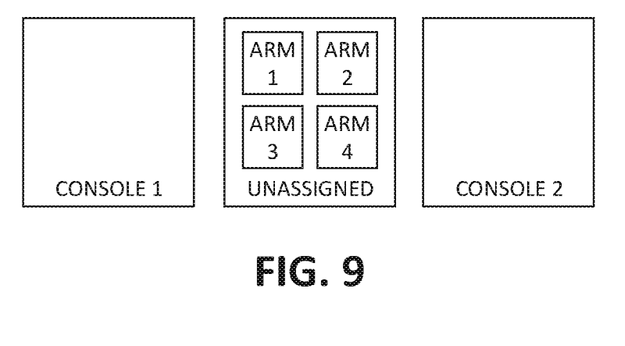
Figure 10:
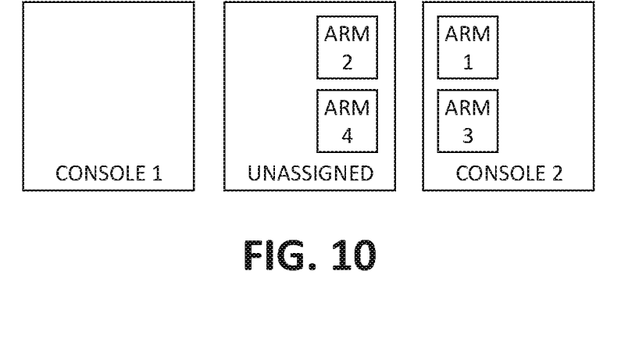

In the event that a selection of either or both of arms 1 or 3 is made by console 2, neither arm can be re-assigned to console 2 due to their assignment to console 1. As shown in FIG. 8, console 1 deselects arms 1 and 3 so that arms 1 and 3, along with arm 4, are now unassigned and are now free to be assigned. In an embodiment, console 2 may receive a request to deselect arm 2 as well so that arm 2, along with arms 1, 3, and 4, is unassigned as illustrated in FIG. 9. Because arms 1 and 3 are unassigned, when console 2 sends a request for arms 1 and 3 to be assigned, both are assigned to console 2 as shown in FIG. 10.

Figure 11:
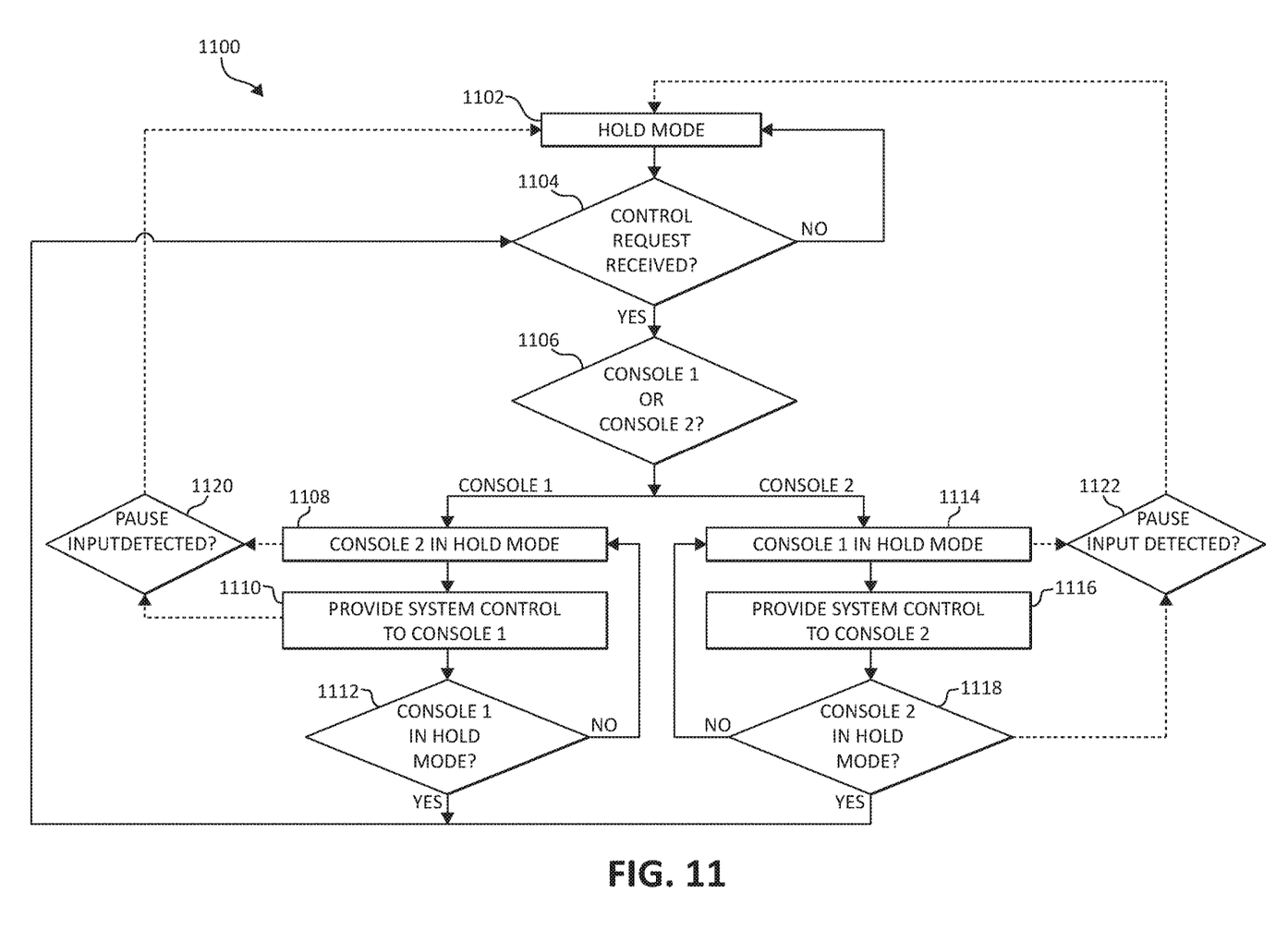
FIG. 11 is a flow diagram of another process for controlling the multi-input robotic surgical system of FIG. 1.

FIG. 11 is a flow diagram of a control process 1100 for operating a multi-input surgical system, in accordance with another embodiment. Here, while one clinician controls arms 236*a-d* of the tower 230, the other clinician cannot gain control unless a pause or release input is detected. Additionally, in an embodiment, the information presented on the displays 244 of each console 240 is substantially identical so that each clinician sees the same information during the process 1100.

With reference to FIGS. 2 and 11, at initiation of the control process 1100, each console 240 is placed in a hold mode, at step 1102. As noted above, the hold mode is a default mode after a power up, a reset, a reboot of the system, or after another initiating operation of the system. During the hold mode, controls associated with the system are not assigned to either console 240. As such, the arms 236*a-d* are unassigned to any console 240, and according to an embodiment, in an event that any of the arms 236*a-d* or other controls are already assigned to a console, the arms 236*-d* are deselected and unassigned and the controls are unassigned to either console.

Next, an input is received at a console indicating that the clinician at the console has requested control of the system at step 1104. In an embodiment, the clinician at one of the consoles 1, 2 uses the input 242 to request control of the system via a keyboard, mouse, joystick or other input 242, such as by typing a selection or selecting an icon or other representation from a drop down menu. In another embodiment, the clinician requests control of the system by selecting an icon representing the arms 236*a-d* which may be selected. According to yet another embodiment, the clinician requests control of the system by depressing a foot pedal or pressing a button on the handle, which may be the input 242. In an embodiment, the consoles 1 and 2 may be unoccupied during the time of selection, and hence, the signal to request control of the system to console 1 occurs remotely from another computer. If no signal has been received or the signal has been received but the clinician has not provided an input within a predetermined time period, the consoles 1, 2 remain in the hold mode at 1102. As part of the request, a determination is made as to whether the control request originates from console 1 or console 2 at step 1106.

If a determination is made that the request originates from console 1, console 2 is either placed or maintained in the hold mode at step 1108, and control of the system is provided to console 1 at step 1110. Although shown in a successive order, step 1108 and step 1110 may be performed concurrently or in reverse order.

A determination is made as to whether console 1 is in hold mode at step 1112. If not, the process 1100 iterates at steps 1108 and 1110 where console 2 is maintained in hold mode while the system control continues to be to console 1. If the determination is made that console 1 is in hold mode, the process 1100 iterates at step 1104 to determine if another input request has been received.

Returning to step 1106, if a determination is made that the input request is received from console 2, console 1 is placed in hold mode at step 1114 and system control is provided to console 2 at step 1116. Similar to steps 1108 and 1110, steps 1114 and 1116 are performed concurrently in an embodiment or alternatively, in reverse order in another embodiment.

At some point while the system is controlled by either console 1 or console 2, a situation may arise during which the clinician at the other console may need to take over system controls. In this regard, the clinician at the console in hold mode may provide a corresponding input, such as depressing a pause button, selecting a pause icon or performing another input-type of action, so that a pause input is detected at console 2 at step 1120 or from console 1 at step 1122 by the system. If the pause input is detected, the process iterates at step 1102, where the consoles 1, 2 are placed in hold mode.

Figure 12:
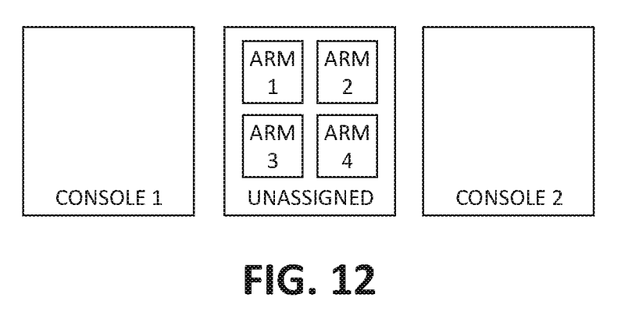
FIGS. 12 through 14 are simplified block diagrams illustrating selection and deselection of arms by the consoles according to the process illustrated in FIG. 11 in accordance with an embodiment
Figure 13:
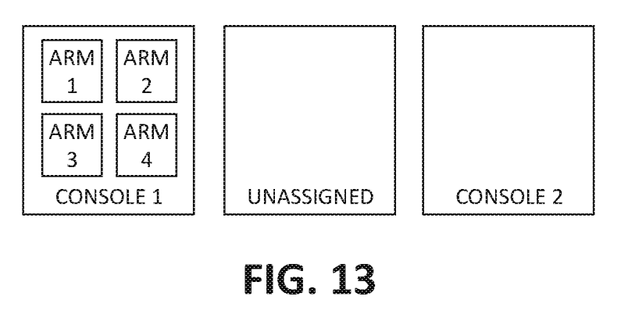
Figure 14:
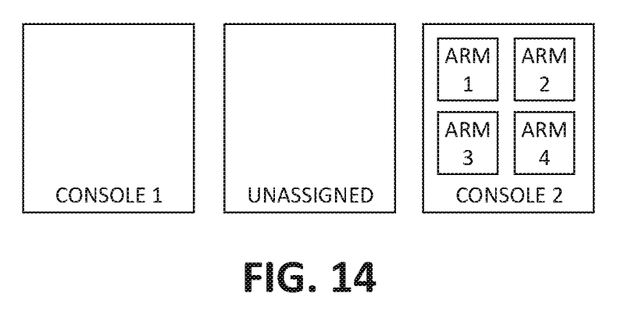

FIGS. 12-14 are simplified block diagrams illustrating the process of providing control to the consoles, for example, by assigning the arms to the consoles, in accordance with an embodiment. FIG. 12 is a representation of the system 10 in a hold mode. Neither console is given control of the system 10, and hence, none of the arms 1-4 are assigned to a console during the hold mode. FIG. 13 is a representation of the system 10 when control of one or more of the arms is requested from console 1. In such case, all of the arms 1-4 are, and hence, system control is, assigned to console 1, and console 2 remains in the hold mode. In an embodiment in which a clinician at console 2 provides a pause input to the system described above, control of the system 10 and all of the arms 1-4 are reassigned to console 2, and console 1 is placed in the hold mode.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, or the like. The controller may also include a memory to store data and/or algorithms to perform a series of instructions.

Any of the herein described methods, programs, algorithms or codes may be converted to, or expressed in, a programming language or computer program. A "Programming Language" and "Computer Program" includes any language used to specify instructions to a computer, and includes (but is not limited to) these languages and their derivatives: Assembler, Basic, Batch files, BCPL, C, C+, C++, Delphi, Fortran, Java, JavaScript, Machine code, operating system command languages, Pascal, Perl, PL1, scripting languages, Visual Basic, metalanguages which themselves specify programs, and all first, second, third, fourth, and fifth generation computer languages. Also included are database and other data schemas, and any other metalanguages. No distinction is made between languages which are interpreted, compiled, or use both compiled and interpreted approaches. No distinction is also made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A method of controlling a robotic surgical system, the robotic surgical system including a plurality of arms, a plurality of consoles, and a controller in communication with the plurality of arms and the plurality of consoles, the method comprising:
   receiving a request for selection of a first arm from the plurality of arms for assignment to a first console of the plurality of consoles;
   in response to the request, determining whether the first arm is already assigned;
   assigning the first arm to the first console, if a determination is made that the first arm is not already assigned;
   determining whether the first arm is to be deselected from a previous assignment, if a determination is made that the first arm is already assigned;
   generating an error message, if a determination is made that the first arm is not to be deselected; and
   deselecting the first arm from the previous assignment and assigning the first arm to the first console, if a determination is made that the first arm is to be deselected.

2. The method of claim 1, further comprising placing the plurality of consoles in a hold mode, prior to receiving the request for selection.

3. The method of claim 1, wherein the placing the plurality of consoles in the hold mode includes determining whether any arm of the plurality of arms is assigned to any of the consoles of the plurality of consoles and deselecting the assigned arms from the consoles.

4. The method of claim 1, further comprising:
   receiving a request for selection of a second arm from the plurality of arms for assignment to a second console of the plurality of consoles;
   in response to the request, determining whether the second arm is already assigned;
   determining whether the second arm is to be deselected, if a determination is made that the second arm is already assigned;
   assigning the second arm to the second console, if a determination is made that the second arm is not already assigned;
   generating an error message, if a determination is made that the second arm is not to be deselected; and
   deselecting the second arm and assigning the second arm to the second console, if a determination is made that the second arm is to be deselected.

5. The method of claim 1, wherein the receiving the request for selection includes receiving the request for selection from the first console.

6. The method of claim 1, wherein the receiving the request for selection includes receiving the request for selection from a remote computer.

7. A robotic surgical system comprising:
   a plurality of linkages moveably coupled to a base;
   a plurality of consoles each including an input device;
   a processing unit in communication with the plurality of consoles and operatively associated with the plurality of linkages; and
   a memory coupled to the processing unit, the memory including instructions that, when executed by the processing unit, causes the processing unit to:
   receive a request for selection of a first linkage from the plurality of linkages for assignment to a first console of the plurality of consoles;
   in response to the request, determine whether the first linkage is already assigned;
   assign the first arm to the first console, if a determination is made that the first linkage is not already assigned;

determine whether the first linkage is to be deselected from a previous assignment, if a determination is made that the first linkage is already assigned;

generate an error message, if a determination is made that the first linkage is not to be deselected; and deselect the first linkage from the previous assignment and assigning the first linkage to the first console, if a determination is made that the first linkage is to be deselected.

8. The robotic surgical system of claim 7, wherein the memory further includes instructions that, when executed by the processing unit, causes the processing unit to place the plurality of consoles in a hold mode, prior to the receiving the request for selection.

9. The robotic surgical system of claim 7, wherein the memory further includes instructions that, when executed by the processing unit, causes the processing unit to place the plurality of consoles in the hold mode including determining whether any arm of the plurality of arms is assigned to any of the consoles of the plurality of consoles and deselecting the assigned arms from the consoles.

10. The robotic surgical system of claim 7, the memory further includes instructions that, when executed by the processing unit, causes the processing unit to:

receive a request for selection of a second arm from the plurality of arms for assignment to a second console of the plurality of consoles;

in response to the request, determine whether the second arm is already assigned;

determine whether the second arm is to be deselected, if a determination is made that the second arm is already assigned;

assign the second arm to the second console, if a determination is made that the second arm is not already assigned;

generate an error message, if a determination is made that the second arm is not to be deselected; and deselect the second arm and assigning the second arm to the second console, if a determination is made that the second arm is to be deselected.

11. The robotic surgical system of claim 7, wherein the receiving the request for selection includes receiving the request for selection from the first console.

12. The robotic surgical system of claim 7, wherein the receiving the request for selection includes receiving the request for selection from a remote computer.

13. A non-transitory computer-readable medium including instructions that, when executed by a processor, causes the processor to:

receive a request for selection of a first linkage from the plurality of linkages for assignment to a first console of the plurality of consoles;

in response to the request, determine whether the first linkage is already assigned;

assign the first arm to the first console, if a determination is made that the first linkage is not already assigned;

determine whether the first linkage is to be deselected from a previous assignment, if a determination is made that the first linkage is already assigned;

generate an error message, if a determination is made that the first linkage is not to be deselected; and deselect the first linkage from the previous assignment and assigning the first linkage to the first console, if a determination is made that the first linkage is to be deselected.

14. The non-transitory computer-readable medium of claim 13, further including instructions that, when executed by the processing unit, causes the processing unit to place the plurality of consoles in a hold mode, prior to the receiving the request for selection.

15. The non-transitory computer-readable medium of claim 13, further including instructions that, when executed by the processing unit, causes the processing unit to place the plurality of consoles in the hold mode including determining whether any arm of the plurality of arms is assigned to any of the consoles of the plurality of consoles and deselecting the assigned arms from the consoles.

16. The non-transitory computer-readable medium of claim 13, further including instructions that, when executed by the processing unit, causes the processing unit to:

receive a request for selection of a second arm from the plurality of arms for assignment to a second console of the plurality of consoles;

in response to the request, determine whether the second arm is already assigned;

determine whether the second arm is to be deselected, if a determination is made that the second arm is already assigned;

assign the second arm to the second console, if a determination is made that the second arm is not already assigned;

generate an error message, if a determination is made that the second arm is not to be deselected; and deselect the second arm and assigning the second arm to the second console, if a determination is made that the second arm is to be deselected.

17. The non-transitory computer-readable medium of claim 13, wherein the receiving the request for selection includes receiving the request for selection from the first console.

18. The non-transitory computer-readable medium of claim 13, wherein the receiving the request for selection includes receiving the request for selection from a remote computer.

19. A method of controlling a robotic surgical system, comprising:

identifying an assignment of control of a plurality of robotic arms of a robotic surgical system to one or more consoles through which at least a part of the robotic surgical system is user controlled;

assigning control of a first of the robotic arms to a first console responsive to receiving a request to do so when the first robotic arm is not identified as assigned to at least one of the consoles;

deassigning control of the first robotic arm from any assigned consoles after a respective assigned console is in a hold mode responsive to receiving the request when the first robotic arm is identified as assigned to at least one of the consoles other than the first console; and waiting until control of the first robotic arm has been deassigned from each of the assigned consoles before assigning control of the first robotic arm to the first console.

* * * * *